(12) United States Patent
Chi-Lam et al.

(10) Patent No.: US 10,760,033 B2
(45) Date of Patent: Sep. 1, 2020

(54) PROCESS OF FORMING 2-(4-ISOBUTYL-2-METHYLPHENYL) PROPANAL

(71) Applicant: GIVAUDAN SA, Vernier (CH)

(72) Inventors: Tse Chi-Lam, Duebendorf (CH); Martin Alan Lovchik, Duebendorf (CH); Simon Ellwood, Rueschlikon (CH); Andreas Goeke, Winterthur (CH)

(73) Assignee: GIVAUDAN SA, Vernier (CH)

( * ) Notice: Subject to any disclaimer, the term of this patent is extended or adjusted under 35 U.S.C. 154(b) by 317 days.

(21) Appl. No.: 15/516,602

(22) PCT Filed: Nov. 12, 2015

(86) PCT No.: PCT/EP2015/076471
§ 371 (c)(1),
(2) Date: Jun. 20, 2018

(87) PCT Pub. No.: WO2016/075257
PCT Pub. Date: May 19, 2016

(65) Prior Publication Data
US 2018/0282662 A1   Oct. 4, 2018

(30) Foreign Application Priority Data
Nov. 12, 2014   (GB) .................................. 1420111.5

(51) Int. Cl.
| | |
|---|---|
| *C07C 45/74* | (2006.01) |
| *C11B 9/00* | (2006.01) |
| *C07C 45/49* | (2006.01) |
| *C07C 17/12* | (2006.01) |
| *C07C 45/62* | (2006.01) |
| *C07C 43/307* | (2006.01) |
| *C07C 49/213* | (2006.01) |
| *C11D 3/20* | (2006.01) |
| *C11D 3/50* | (2006.01) |

(52) U.S. Cl.
CPC ............ *C11B 9/0061* (2013.01); *C07C 17/12* (2013.01); *C07C 43/307* (2013.01); *C07C 45/49* (2013.01); *C07C 45/62* (2013.01); *C07C 45/74* (2013.01); *C07C 49/213* (2013.01); *C11D 3/2072* (2013.01); *C11D 3/50* (2013.01); *C07C 2601/16* (2017.05)

(58) Field of Classification Search
CPC ......... C07C 45/59; C07C 45/62; C07C 45/74; C07C 43/307; C11B 9/0061
See application file for complete search history.

(56) References Cited

U.S. PATENT DOCUMENTS

| | | |
|---|---|---|
| 4,486,607 A | 12/1984 | Webb |
| 5,208,384 A | 5/1993 | Hermeling |
| 5,527,769 A | 6/1996 | Winter et al. |

FOREIGN PATENT DOCUMENTS

| | | |
|---|---|---|
| GB | 1057360 A2 | 2/1967 |
| WO | 2006077305 A1 | 7/2006 |
| WO | 2014180945 A1 | 11/2014 |
| WO | 2014180952 A1 | 11/2014 |

OTHER PUBLICATIONS

International Search Report and Written Opinion of the International Searching Authority for corresponding application PCT/EP2015/076471 dated Feb. 4, 2016.
G. Skouroumis, et al., "Synthesis of 1,3,4,5-Tetrahydro-2-Benzoxepin Derivatives as Conformationally Restricted Analogues of Cyclmenaldehyde-Type Compounds and as Intermediates for Highly Ofour-Active Homologues", Helvetica Chimica Acta, Verlag Helvetica Chimica Acta, CH, vol. 79, No. 4, Jan. 1, 1996, pp. 1095-1109.
G. Wolf, et al., "Preparation of Polycyclic Aromatic Hydrocarbons as Potential Carcinogens 1", Journal of American Chemical Society, vol. 75, No. 11, Jun. 1953, pp. 2673-2678, US.
A. Matsuo, et al., "Structures of ent-herbertane sesquiterpenoids displaying antifingal properties from the liverwort Herberta adunca", Journal of the Chemical Society, Perkin Transactions Jan. 1, 1986, pp. 701-710, GB.
D. Nasipuri, et al., "Polycyclic Systems. Part 19. Synthesis of 8-isobutyl-10-methyl-11H-indeno[2,1-a] phen minor dehydration product of cholesterol", Journal of the Chemical Society, Perkin Transactions Jan. 1, 1979, pp. 3034-3036, GB.

*Primary Examiner* — Sikarl A Witherspoon
(74) *Attorney, Agent, or Firm* — Norris McLaughlin PA

(57) ABSTRACT

The regio-selective functionalization of a dialkyl benzene compound

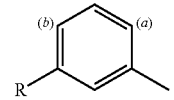

wherein the ratio of the compound functionalized at position (a) to the compound functionalized at the position (b) is at least 70:30, more particularly at least 80:20, still more particularly at least 85:15, and still more particularly at least 90:10, characterised in that the substituent R is an isobutyl group.

13 Claims, 1 Drawing Sheet

PROCESS OF FORMING 2-(4-ISOBUTYL-2-METHYLPHENYL) PROPANAL

Figure 1:
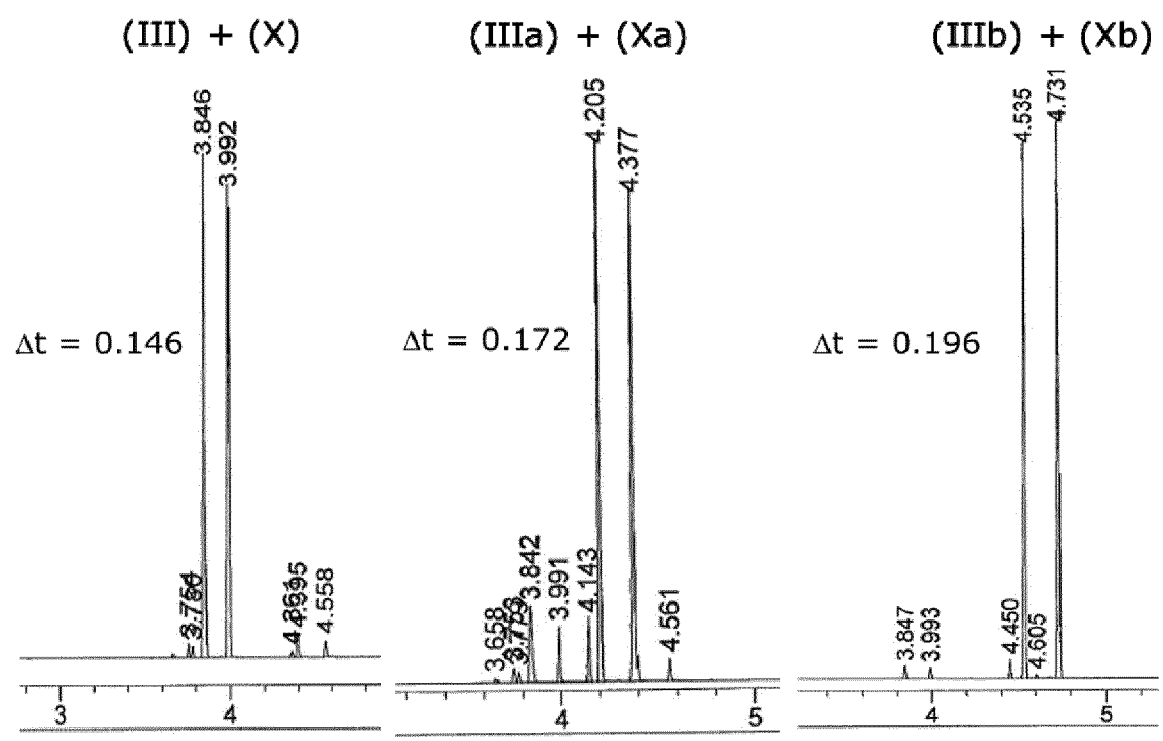

This is an application filed under 35 USC 371 of PCT/EP2015/076471 filed 12 Nov. 2015, which in turn claims the benefit of GB 1420111.5. The present application claims all available priority benefits to the foregoing applications, and also incorporates by reference the entirety of their disclosures as if set forth herein.

This invention relates generally to methods of preparing perfumery raw materials and to key intermediates used in, or prepared during, such methods.

Compounds having muguet odour characteristics are very sought after as perfume ingredients. These compounds are important ingredients in floral bases and can act as harmonizers across many types of fragrance creations. Compounds of this type are used widely in personal care and consumer care products, as well as in fine perfumery, to generate pleasant odours or to mask unpleasant odours.

An excellent perfume ingredient widely valued for its muguet odour note is Lilial™ or 3-(4-tert-butylphenyl)-2-methylpropanal (CAS 80-54-6). This compound has found wide use in fine perfumery as well as in personal and household care products. However, its use is controversial in view of recent findings that it exhibits toxic effects on the reproductive organs of male rats and dogs. No effects were found in studies with mice, guinea-pigs and primates, nevertheless, under the Global Harmonized System (GHS) classification system this compound is classified as a CMR2 material. For CMR category 2 materials, it is necessary to establish that quantities proposed for use are harmless to consumers. In view of the regulatory status of Lilial™ it is being replaced with other perfume ingredients.

WO2010105 873 addresses the problem of replacing Lilial™, the proposed solution residing in the use of mixtures of known ingredients commonly found on the perfumers' palette in order to recreate characteristics substantially similar to those of Lilial™.

Likewise, WO2009027957 proposes a solution residing in the formulation of combinations of known perfume ingredients from the perfumers' palette.

WO2013045301 also proposes a solution to Lilial™ replacement, which resides in the selection of mixtures of ingredients including the compound Lilyflore™ and a certain indanyl propanal compound, in combination with other secondary perfuming ingredients.

The applicant recently found a novel compound that can be employed as a perfume ingredient in perfume compositions and fine fragrances and consumer products to impart desirable muguet odour characteristics to said compositions, fragrances and products. More particularly, the novel compound possesses odour characteristics, which may be perceived and recognised by perfumers as being very reminiscent of the odour of Lilial™. Still further, the novel compound is not affected by any of the toxicity issues that surround Lilial™. As such, this novel compound can serve as a simple replacement for Lilial™.

The novel compound, which is described in co-pending patent application PCT/EP/2014059427 (herein incorporated by reference in its entirety is defined by the formula (I)

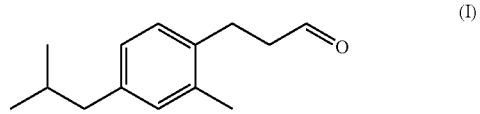

(I)

The compound of formula (I) possesses substantially similar odour characteristics and performance characteristics at least as good as Lilial™. As such, and in contradistinction to the prior art proposals related to Lilial™ replacement based on mixtures of known ingredients, the present invention provides for a Lilial™ replacement based on a single compound. This has the obvious advantage of representing a cost-effective solution to the replacement problem, but it also makes the perfumers' creative process simpler.

The regulatory issues surrounding Lilial™ are born from the fact that it is enzymatically degraded in rats and dogs to tert-butyl benzoic acid (t-BBA). Tertiary butyl benzoic acid, is known to inhibit glucose synthesis and fatty acid synthesis in vitro (McCune et al, Arch Biochem Biophys (1982) 214 (1): 124-133).

tert-butyl benzoic acid is known to cause testicular effects in male rats (Hunter et al. Food Cosmet. Toxicol. 1965, 3: 289-298; Cagen et al. J. Am. Coll. Toxicol. 1989, 8 (5): 1027-1038).

The applicant recently found that the compound of formula (I) was not susceptible to enzymatic degradation to its benzoic acid derivative. Although the applicant does not intend to be bound by any particular theory, it is believed that the benzoic acid derivative is a key intermediate from which a cascade of metabolic activity occurs, leading to male reproductive toxicity and reduced sperm formation in male rats. More specifically, it is believed that tert-butyl benzoic acid and related branched alkyl substituted benzoic acids bind to Co-enzyme A in rat cells to form a sulphur ester with this co-factor. In turn, it is believed that this sulphur ester inhibits other enzymes that are responsible for fatty acid metabolism within the rat cells, and it is this interference with CoA dependent reactions which leads to the observed reproductive toxicity.

The applicant's surprising discovery that aryl-substituted alkanal compounds containing a substituent, e.g. a methyl substituent, on the ring at a position ortho to the group bearing the aldehyde functionality are not susceptible to enzymatic degradation to their corresponding benzoic acid derivatives, provided an insight heretofore not know in the art. This insight has enabled the applicant to develop the compound of formula (I), and structurally related derivatives thereof, and thereby add to the palette of perfumery ingredients, novel perfume ingredients that are not only useful in their own right, but are suitable as replacements for Lilial™.

However, despite the attractiveness of the compound of formula (I) (and structurally related derivatives) as a perfumery material, and despite its relatively simple chemical structure, the applicant found that it is complicated and costly to prepare using chemistry that is industrially scalable. The complications derive from the fact that the compound is a tri-substituted aryl compound. On the one hand, tri-substituted aryl starting materials are scarce and expensive, whereas on the other hand, functionalizing an aromatic ring with three substituents generally requires lengthy and complex syntheses.

Accordingly, there remains a need to provide an economical and industrially scalable synthesis into the compound of formula (I).

During the course of its research the applicant consider a large number of possible synthetic routes into the compound of formula (I). It was determined that the methyl substituent could not be added to the ring during the synthesis of compound (I) in an economic manner. The methyl substituent would have to be present in a readily available starting material. m-xylene represented such a cheap and readily available starting material, and it could be easily homologized at one of its methyl substituents to provide a key intermediate (compound II) in a process of forming a compound of formula (I). This key intermediate would need to be functionalised on the ring if an economically feasible and industrially scalable synthesis was to be realised.

FIG. 1 depicts a comparison of the increasing differences of retention times in GC separation which are indicative of an improved separation by distillation.

Accordingly, the invention provides in a first aspect a method of regio-selectively functionalizing an alkyl toluene compound (II)

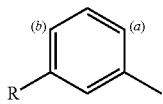

at position (a) on the ring, wherein the substituent R is an isobutyl group.

In another aspect of the present invention there is provided a process of forming a compound according to the formula (I)

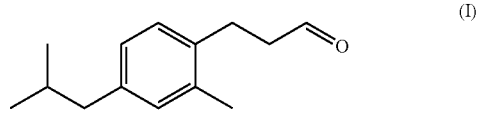

comprising the step of regio-selectively functionalizing 3-methyl-1-isobutyl benzene (compound II)

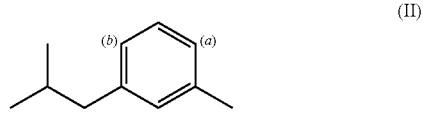

at the position (a) on the ring.

By "regio-selectively" is meant that the functionalization is directed predominantly at the position (a) on the ring rather than the position (b). More particularly, "regio-selectively" means that the ratio (a):(b) is at least 70:30, more particularly at least 80:20, still more particularly at least 85:15, more particularly still at least 90:10.

In yet another aspect of the present invention there is provided the use of 3-methyl-1-isobutyl benzene (compound II) as an intermediate in the synthesis of compound (I).

As stated hereinabove, the applicant found that it is critical for an economically feasible and industrially scalable process into the compound (I) that the methyl group is already located on an available starting material. This finding determines that compound (II) (3-methyl-1-isobutyl benzene) is a key intermediate in any process, and that the functionalization of this compound must proceed with such high regio-selectivity.

And yet, the idea of preparing the compound of formula (I) via the key intermediate, compound (II) is counterintuitive because the prior art articulates a prejudice against doing precisely this. Specifically, Rao et al in the Indian Journal of Chemistry vol. 16B, May 1978 introduces aldehyde functionality into 3-methyl-1-isobutyl benzene (III e in that paper). The compound produced was 2-isobutyl-4-methylbenzaldehyde (III g), indicating that the isobutyl group directs the aldehyde functionality into the ortho-position and not the para-position relative to the iso-butyl group. In other words, the isobutyl group does not promote high regio-selectivity for the position para-relative to it.

Applicant's own findings, which are summarized in Table 1 below, surprisingly are in disagreement with Rao et al. In the carbonylation of 1-butyl-3-methyl benzene compounds in the presence of carbon monoxide (approximately 40 bar) and triflic acid, the tertiary-butyl and sec-butyl ring substituents are found not to be at all effective at selectively directing the carbonylation to the ring position para- to the butyl substituent. Whereas, the n-butyl substituent, which is substantially more effective than the tertiary-butyl and sec-butyl substituents, is less effective when compared with the iso-butyl substituent.

TABLE 1

| Butyl substituent of 1-butyl-3-methyl benzene | Rate of conversion after 1 h in % | Aldehyde Ratio (a):(b) |
|---|---|---|
| n-Butyl | 100 | 2.58 |
| sec-Butyl | 90 | 1.17 |
| iso-Butyl | 100 | 3.00 |
| tert-Butyl | 80 | no identifiable aldehyde |

In accordance with the present invention 3-methyl-1-isobutyl benzene (compound II) may be prepared from 3-isobutyl-1-methylcyclohex-1-ene (compound (Ia) according to known methods. In particular, (Ia) can be dehydrogenated under reduced pressure using a palladium catalyst, immobilized on aluminium oxide or carbon. The dehydrogenation can be carried out at room temperature or elevated temperatures, preferably at 200° C.

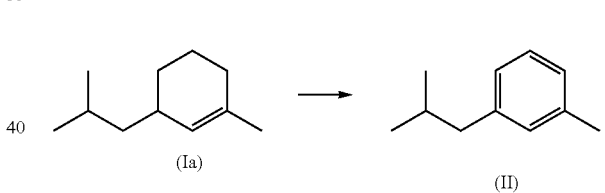

The choice of functional group that can be introduced into 3-methyl-1-isobutyl benzene (compound II) at the para position (relative to the isobutyl group) can be quite varied.

Introduction of benzaldehyde functionality regio-selectively is a preferred embodiment of the invention. Introduction of this functionality can be achieved in several ways. One method is to first chloromethylate compound (II), before converting the 1-chloromethyl-2-methyl-4-isobutyl-benzene into 2-methyl-4-isobutyl benzaldehyde. However, for reasons related to procedural efficiency, chloromethylation of compound (II) is not a preferred embodiment of the present invention.

Direct introduction of benzaldehyde functionality into the ring by carbonylation is a preferred embodiment of the invention.

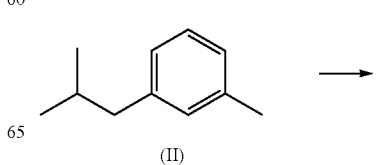

-continued

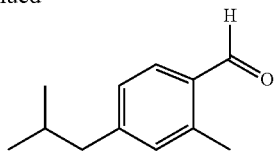

(III)

In a particular embodiment of the invention, this reaction may be carried out in 6.8 molar equivalents of triflic acid under about 40 to 60 atmospheres of carbon monoxide in an autoclave. The carbonylation will provide a mixture of regio-isomers, which may contain 70%, and more particularly 80% (or even higher amounts) of compound (III).

Alternatively, the reaction can be carried out in $HF/BF_3$ under conditions generally known in the art. This reaction is frequently referred to as "Mitsubishi" chemistry.

A representative example of Mitsubishi chemistry is described in U.S. Pat. No. 3,962,343, which is incorporated herein by reference.

In another embodiment of the invention, the compound of formula (II) can be brominated under reaction conditions generally known in the art

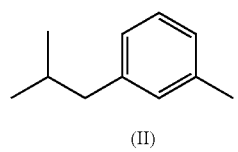

(II)

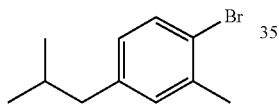

(IV)

Operative reaction conditions are treatment of (II) neat with one molar equivalent bromine in the presence of 0.05 molar equivalents of iron powder at 10° C.

In yet another embodiment of the invention, the compound of formula (II) can be directly converted into the compound of formula (I)

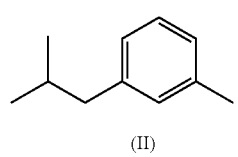

(II)

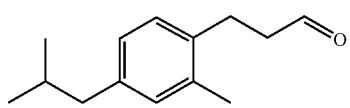

(I)

Reaction conditions for this transformation are generally known in the art, and may proceed with the reaction of compound (II) with titanium tetrachloride and a compound of the formula (V) in dichloro methane at −70° C. Hydrolysis of the intermediate enol acetate with dilute sulfuric acid affords (VI) to 40% in a mixture of regio isomers.

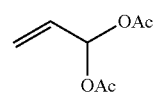

(V)

Compound of formula (III) can be converted into compound (VI) using Muller Conradi-Pieroh conditions, generally known in the art.

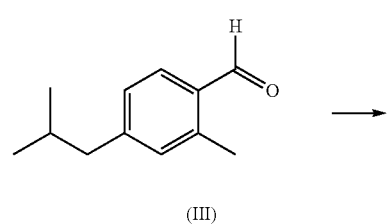

(III)

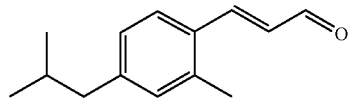

(VI)

Particular reaction conditions include converting the benzaldehyde (III) to the dimethyl acetal by treatment with trimethyl orthoformate, followed by reaction with ethyl vinyl ether in the presence of catalytic boron trifluoride etherate at room temperature. The intermediate ethoxy methoxy acetals were hydrolyzed in the presence of 5% HCl to afford (VI).

Another advantage attendant with the inclusion of the methyl substituent in the starting material is that, unlike the solid 4-isobutyl benzaldehyde used, for example, as a starting material in the synthesis of the well-known fragrance ingredient Bourgeonal®, the presence of the methyl substituent in compound (III) renders the compound a liquid, which makes it easier to handle on an industrial scale.

Thereafter, the compound of formula (VI) can be hydrogenated to provide the compound of formula (I). Hydrogenation conditions are generally well known in the art, and include catalytic hydrogenation of the double bond in the propenal side chain over palladium on carbon 5% at 500 mbar pressure.

Compound (IV) described hereinabove can be further converted in accordance with the reaction schemes

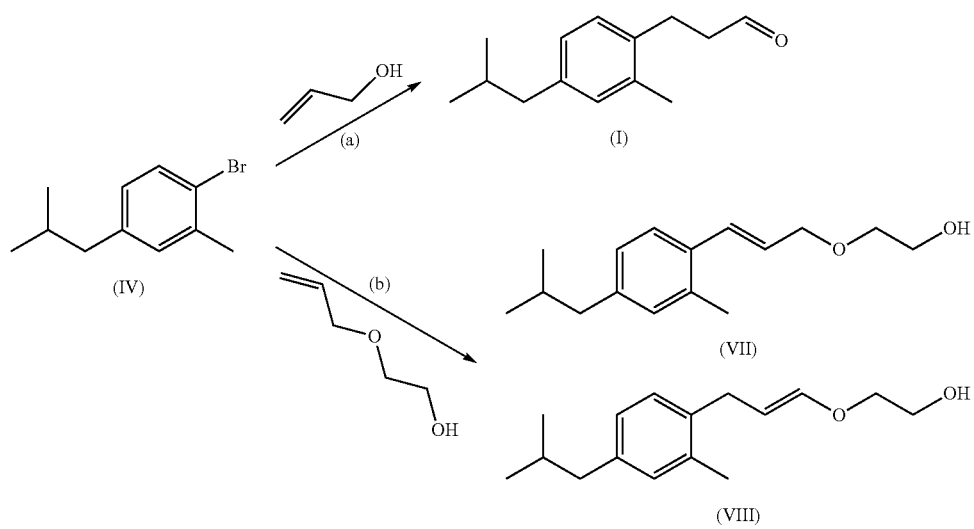

Reaction scheme (a) describes the conversion of compound (IV) into compound (I). This reaction may be carried out by the Heck reaction of (IV) with allyl alcohol, catalysed by palladium in the presence of a secondary amine followed by oxidation of the resulting propanol side chain, using conditions generally known in the art, to afford compound (I).

Reaction scheme (b) describes a similar process of reacting an allyl ether with a compound of the formula (IV) under Heck conditions to afford a mixture of compounds (VII) and (VIII). The skilled person would expect that acid hydrolysis of the mixture of compound (VII) and (VIII) would result in a mixture of compound (IX) and the desired compound (I), and as such, a synthetic route proceeding through this mixture would, at first sight, appear unpromising.

However, to applicant's surprise, both compounds (VII) and (VIII) were converted to compound (I) upon acidic hydrolysis suggesting that (VII) underwent acid mediated double bond migration to (VIII) before hydrolysing to give compound (I).

Accordingly, the invention provides in another of its aspects a method of forming a compound of formula (I), comprising the step of forming the mixture of compound (VII) and (VIII).

When compound (III) is obtained in a mixture with regio-isomers, in particular in mixture with 2-isobutyl-4-methyl benzaldehyde (X), it is difficult to separate them by distillation. However, the separation of compound (III) can be facilitated by distillation of the corresponding dialkylacetals, preferably the corresponding dimethyl acetals (IIIa+Xa) or diethyl acetals (IIIb+Xb). This is demonstrated by the comparison of the increasing differences of retention times in GC separation which are indicative of an improved separation by distillation (FIG. 1).

Therefore, the corresponding dialkylacetal of compound of formula (III), in particular the diethylacetal of compound of formula (III), which is compound (IIIb), is a useful intermediate for preparation of desired compound of formula (I), and constitutes a further aspect of the present invention.

The mixture of regio-isomers (III) and (X) is converted in a first step a) to the corresponding mixture of diethyl acetals (IIIb+Xb) by treatment with triethyl orthoformate and catalytic amounts of $BF_3 \cdot Et_2O$. In a second step b), after neutralization of the crude reaction mixture, a distillation is performed to obtain the diethyl acetal (IIIb) in essentially pure form. The compound of formula (IIIb) can be either hydrolysed to the compound of formula (III), or converted directly to the compound of formula (VI) in a similar manner as described above.

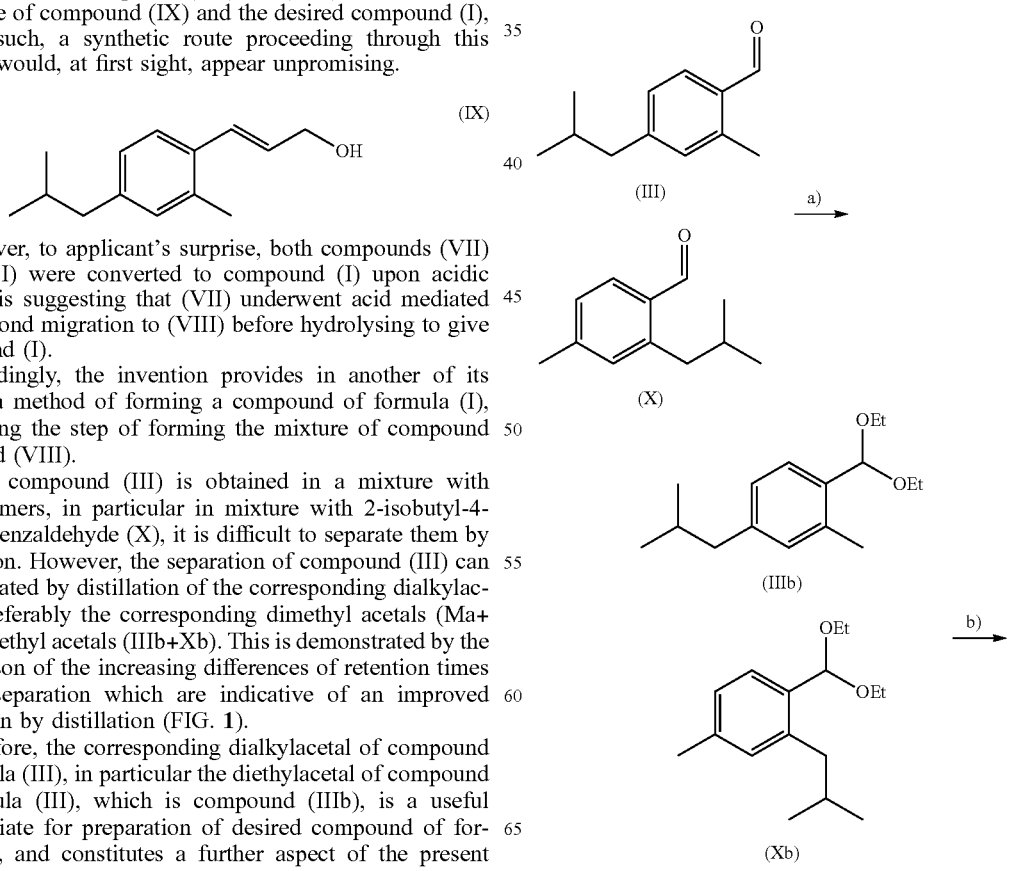

-continued

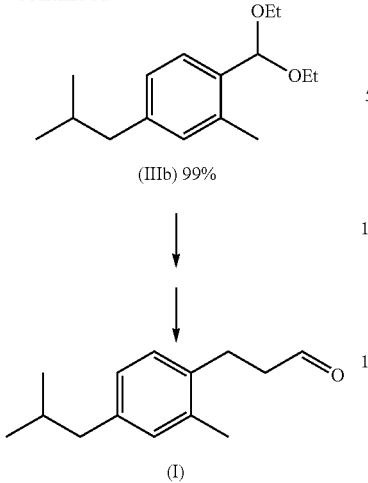

Alternatively, BF$_3$.Et$_2$O can be replaced by p-Toluenesulfonic acid (pTSA), and after removal of the undesired isomer, the Müller-Cunradi reaction can be performed even in the presence of pTSA. —Therefore the acetal formation, distillation and Müller-Cunradi reaction could be performed as a "one-pot" process.

Accordingly, in a further aspect, the invention provides a method to purify or separate compound (III) and thereby to enhance the purity of the products obtained in further reactions, in particular the compound of formula (I).

There now follows a series of examples that serve to further illustrate the invention.

EXAMPLE 1: SYNTHESIS OF 3-(4-ISOBUTYL-2-METHYLPHENYL)PROPANAL

A) 3-isobutyl toluene (II)

A mixture of freshly distilled 3- and 5-isobutyl-1-methylcyclohex-1-ene (700 g, 4.6 mol) was passed vertically through a glass tube (2×50 cm) filled with 100 g of palladium on alumina pellets (Aldrich, art. 205745) and heated to 200° C. The cyclohexene was passed though the column at a rate of 2 ml/min at 32 mbar. The crude (II) was condensed and collected in a recipient at the bottom of the column. The product, containing 90% (II) and 10% 1-isobutyl-3-methylcyclohexane was purified by distillation (bp. 105° C., 88 mbar) over a 50 cm packed column to afford pure (II) (566 g, 83% yield).

$^1$H-NMR (400 MHz, CDCl3): δ=7.24 (dd, J=7.58 Hz, 1H), 7.05 (m, 3H), 2.52 (d, J=7.07 Hz, 2H), 2.41 (s, 3H), 1.94 (m, 1H), 0.99 (d, J=6.82 Hz, 6H) ppm. $^{13}$C-NMR (400 MHz, CDCl3): δ=141.7 (s), 137.6 (s), 130.0 (d), 128.0 (d), 126.4 (d), 126.2 (d), 45.5 (t), 30.3 (d), 22.5 (2q), 21.5 (q) ppm. GC/MS (EI): 148 (M$^+$, 26), 106 (42), 105 (100), 103 (8), 91 (18), 79 (7), 77 (11), 43 (8), 41 (8), 39 (8).

B) 2-methyl-4-isobutyl bromide (IV)

The reactor was flushed with nitrogen and (II) (5440 g, 36.7 mol) was added. Iron powder (102 g, 1.8 mol) and iodine (1 g) was added while stirring. The mixture was cooled to 10° C. and dibromine (5860 g, 36.7 mol) was added drop wise over 6 hours at 10° C. During the addition one molar equivalent of hydro bromic acid is produced that must be absorbed by appropriate means. Following the addition the reaction was stirred for 1 h at room temperature and then washed with 10 l of NaOH 2M. The mixture was extracted twice with hexane, then the organic layers were combined, washed with water and brine and concentrated in vacuo. Short path distillation (120° C., 8 mbar) afforded (IV) (4580 g, 55% yield).

$^1$H-NMR (400 MHz, CDCl3): δ=7.46 (d, J=8.07 Hz, 1H), 7.06 (s, 1H), 6.87 (d, J=8.07 Hz, 1H), 2.45 (d, J=7.09 Hz, 2H), 2.42 (s, 3H), 1.88 (m, 1H), 0.95 (d, J=6.60 Hz, 6H) ppm. $^{13}$C-NMR (400 MHz, CDCl3): δ=141.0 (s), 137.2 (s), 132.0 (d), 131.7 (d), 128.3 (d), 122.0 (s), 44.7 (t), 30.1 (d), 22.9 (q), 22.3 (2q) ppm. GC/MS (EI): 228 (M$^+$, 20), 226 (M$^+$, 20), 186 (21), 185 (97), 184 (23), 183 (100), 105 (19), 104 (14), 103 (17), 77 (13).

C) 2-methyl-4-isobutyl benzaldehyde (III)

Magnesium turnings (171 g, 7 mol) was placed in a reactor and covered with THF. A small amount (6 ml) of (IV) was added and the reaction initiated by gentle heating. The remaining (IV) (1589 g, 7 mol) was mixed with THF (3 l) and added drop wise while maintaining a gentle reflux (70-85° C.) without external heating. After the addition was complete, the mixture was stirred at reflux for an additional hour. The reaction mixture was cooled to 10° C. and dimethyl formamide (566 g, 7.7 mol) was added drop wise over 1 hour keeping the temperature below 30° C. The reaction mixture was stirred for 1 hour and then quenched with ice cold HCl (2M). The mixture was extracted with hexane, the organic layers were combined and washed with water and brine. The solution was dried over MgSO$_4$ and concentrated in vacuo. Distillation over a 100 cm packed column (b.p. 105° C., 2.5 mbar) gave pure (III) (592 g, 48% yield).

$^1$H-NMR (400 MHz, CDCl3): δ=10.22 (s, 1H), 7.71 (d, J=7.82 Hz, 1H), 7.14 (d, J=7.58 Hz, 1H), 7.04 (s, 1H), 2.65 (s, 3H), 2.50 (d, J=7.34 Hz, 2H), 1.91 (m, 1H), 0.92 (d, J=6.85 Hz, 6H) ppm. $^{13}$C-NMR (400 MHz, CDCl3): δ=192.3 (d), 148.2 (s), 140.5 (s), 132.6 (d), 132.3 (d), 132.2 (s), 127.1 (d), 45.4 (t), 30.1 (d), 22.4 (2q), 19.6 (q) ppm. GC/MS (EI): 176 (M$^+$, 53), 134 (100), 133 (38), 106 (14), 105 (70), 103 (14), 91 (37), 77 (19), 43 (30), 41 (14).

D) 3-(4-isobutyl-2-methyl phenyl)propen-2-al (VI)

A reactor was charged with (III) (1 kg, 5.68 mol), methanol (400 ml) and trimethyl orthoformate (900 g, 8.49 mol). The reaction mixture was cooled to −10° C. and hydrochloric acid (37%, 1 g) was added. The reaction was exothermal and the temperature was allowed to rise to 25° C., the mixture was stirred for 30 minutes. The reaction was quenched with sodium acetate (20 g) and the volatiles were removed by distillation under vacuum. The residual acetal was charged into a second reactor and boron trifluoride etherate (1 g) was added and ethyl vinyl ether (538 g, 7.5 mol) was added drop wise over 4 hours while maintaining the temperature at 25-30° C. The reaction mass was quenched with saturated sodium carbonate (500 ml). The resulting crude methoxy ethoxy acetals were hydrolysed with water (500 ml) containing hydrochloric acid (37%, 50 g) at 90° C. for 5 hours. The intermediate (VI) was short path distilled at 120° C.

$^1$H-NMR (400 MHz, CDCl3): δ=9.87 (s, 1H), 7.78 (d, J=15.89 Hz, 1H), 7.55 (d, J=8.31 Hz, 1H), 7.06 (m, 1H), 6.96 (m, 1H), 6.68 (m, 1H), 2.50 (s, 2H), 2.49 (s, 3H), 1.88 (m, 1H), 0.94 (d, J=6.60 Hz, 6H) ppm. $^{13}$C-NMR (400 MHz, CDCl3): δ=194.0 (d), 150.4 (d), 145.5 (s), 137.8 (s), 131.9

(d), 130.3 (s), 128.7 (d), 127.5 (d), 126.7 (d), 45.3 (t), 30.1 (d), 22.40 (2q), 19.8 (q) ppm. GC/MS (EI): 202 (M+, 8), 187 (42), 159 (31), 145 (100), 141 (13), 131 (30), 129 (20), 128 (22), 116 (18), 115 (34).

E) 3-(4-Isobutyl-2-methyl phenyl)propanal (I)

The distilled (VI) was charged into an autoclave and isopropanol (200 ml) was added. The unsaturated aldehyde was hydrogenated over palladium (5%) on carbon at 0.5 bar hydrogen pressure. The mixture was filtrated and concentrated in vacuo. The crude product was purified by distillation over a 50 cm packed column (b.p. 116° C., 0.05 mbar) to provide the product (I) (926 g, 80% yield based on (III)).

Odor: floral, aldehydic, green, rubbery, Lilial, watery.
1H-NMR (400 MHz, CDCl3): δ=9.88 (t, J=1.5 Hz, 1H), 7.07 (d, J=7.6 Hz, 1H), 7.0-6.95 (m, 2H), 2.98-2.93 (m, 2H), 2.79-2.74 (m, 2H), 2.46 (d, J=7.1 Hz, 2H), 2.33 (s, 3H), 1.95-1.82 (m, 1H), 0.95 (d, J=6.6 Hz, 6H) ppm. 13C-NMR (400 MHz, CDCl3): δ=202.2 (d), 140.2 (s), 136 (s), 135.9 (s), 131.6 (d), 128.6 (d), 127.3 (d), 45.4 (t), 44.6 (t), 30.6 (d), 25.5 (t), 22.9 (q), 19.7 (q) ppm. GC/MS (EI): 204 (M+, 23), 161 (100), 147 (26), 143 (49), 119 (84), 118 (34), 117 (33), 115 (33), 105 (59), 91 (36).

EXAMPLE 2: SYNTHESIS OF 1-(DIETHOXYMETHYL)-4-ISOBUTYL-2-METHYLBENZENE (IIIB)

A mixture 85:15 of (III) and (X) (200 g, 1.13 mol) was placed in a reactor and trifluoroborane THF complex (1 g, 0.01 mol) was added. Triethyl orthoformate (200 g, 1.35 mol) was added over 20 minutes at 25-30° C. while cooling with an ice bath. The dark red reaction mixture was stirred for 10 minutes and then triethylamine (2 ml, 0.01 mol) was added and the mixture containing (IIIb) and (Xb) was distilled over a 30 cm column filled with wire mesh cylinders (2×3 mm) to afford pure (IIIb) (b.p 100° C., 2.6 mbar, 197 g, 69% yield)

1H-NMR (400 MHz, CDCl3): δ=7.46 (d, J=7.83 Hz, 1H), 6.96 (dd, J=7.58, 1.47 Hz, 1H), 6.93 (s, 1H), 5.54 (s, 1H), 3.56 (m, 4H), 2.42 (d, J=7.09 Hz, 2H), 2.35 (s, 3H), 1.84 (dt, J=13.39, 6.88×(2) Hz, 1H), 1.22 (t, J=7.09×(2) Hz, 6H), 0.89 (d, J=6.60 Hz, 6H) ppm. 13C-NMR (400 MHz, CDCl3): δ=141.7 (s), 135.8 (s), 134.1 (s), 131.3 (d), 126.2 (2d), 100.2 (d), 61.3 (2t), 45.1 (t), 30.2 (d), 22.4 (2q), 18.9 (q), 15.25 (2q) ppm. GC/MS (EI): 250 (M+, 1), 206 (15), 205 (100), 177 (27), 162 (8), 134 (10), 105 (22), 103 (8), 91 (13), 57 (10), 29 (7).

The invention claimed is:

1. A process of regio-selective functionalization of a dialkyl benzene compound according to the following formula

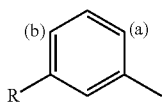

wherein the ratio of the compound functionalized at position (a) to the compound functionalized at the position (b) is at least 70:30, and wherein the substituent R is an isobutyl group,
wherein the process include a carbonylation reaction which introduces a benzaldehyde functionality into the position (a), and
wherein the carbonylation reaction is carried out using HF/BF3 and carbon monoxide.

2. A process of forming a compound according to the following formula (I)

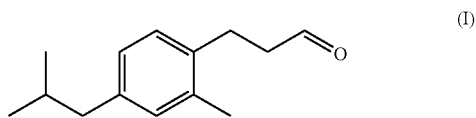

comprising the step of:
regio-selectively functionalizing a dialkylbenzene compound

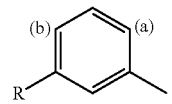

wherein the ratio of the compound functionalized at position (a) to the compound functionalized at the position (b) is at least 70:30, and wherein the substituent R is an isobutyl group.

3. A process of forming a compound of the following formula (I)

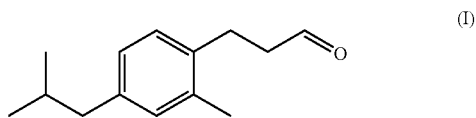

comprising the steps of: —

A)

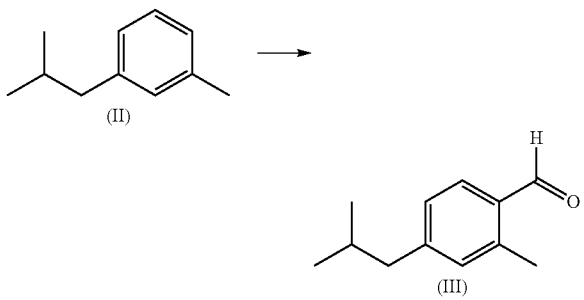

B)

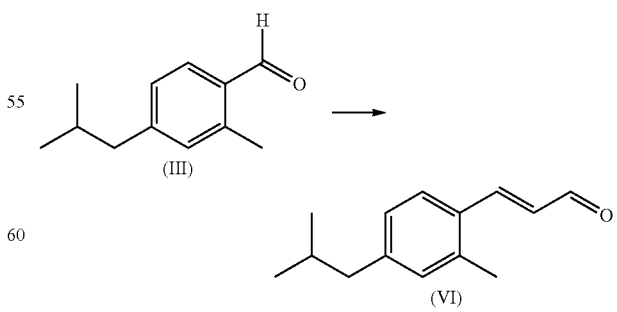

and subsequently,
C) the hydrogenation of compound (VI) to provide compound (I).

4. The process of claim 3, wherein compound (III) is converted to the corresponding dialkylacetal for purification and is then further converted into compound (I).

5. A compound of the following formula IIIb

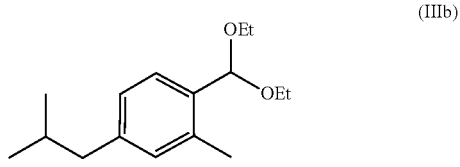 [SMILES: CCOC(OCC)c1ccc(CC(C)C)cc1C]

(IIIb)

formed in a process of forming a compound of the following formula (I)

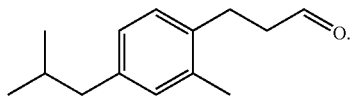

(I)

6. The process of claim 4, wherein the corresponding dialkylacetal is compound IIIb.

7. The process of claim 1, wherein the wherein the ratio of the compound functionalized at position (a) to the compound functionalized at the position (b) is at least 80:20.

8. The process of claim 7, wherein the wherein the ratio of the compound functionalized at position (a) to the compound functionalized at the position (b) is at least 85:15.

9. The process of claim 8, wherein the wherein the ratio of the compound functionalized at position (a) to the compound functionalized at the position (b) is at least 90:10.

10. The process of claim 2, wherein the wherein the ratio of the compound functionalized at position (a) to the compound functionalized at the position (b) is at least 80:20.

11. The process of claim 10, wherein the wherein the ratio of the compound functionalized at position (a) to the compound functionalized at the position (b) is at least 85:15.

12. The process of claim 11, wherein the wherein the ratio of the compound functionalized at position (a) to the compound functionalized at the position (b) is at least 90:10.

13. The process of claim 2, wherein the step of regioselectively functionalizing a dialkylbenzene compound is a carbonylation, a chloromethylation, a bromination or a direct conversion into the compound of formula (I).

* * * * *